US011213248B2

(12) United States Patent
McDonald et al.

(10) Patent No.: US 11,213,248 B2
(45) Date of Patent: Jan. 4, 2022

(54) APPARATUS FOR MONITORING PREGNANCY OR LABOUR

(71) Applicants: The University of Sydney, Sydney (AU); Sydney Local Health District, Camperdown (AU)

(72) Inventors: Sarah Catherine McDonald, Wanniassa (AU); Graham Brooker, Kirrawee (AU); Jonathan Hyett, Riverview (AU); Hala Phipps, Cronulla (AU); Javier Martinez, Rooty Hill (AU)

(73) Assignee: Baymatob Pty Ltd, Broadway (AU)

( * ) Notice: Subject to any disclaimer, the term of this patent is extended or adjusted under 35 U.S.C. 154(b) by 270 days.

(21) Appl. No.: 16/467,879

(22) PCT Filed: Dec. 7, 2017

(86) PCT No.: PCT/AU2017/051346
§ 371 (c)(1),
(2) Date: Jun. 7, 2019

(87) PCT Pub. No.: WO2018/102874
PCT Pub. Date: Jun. 14, 2018

(65) Prior Publication Data
US 2020/0085365 A1    Mar. 19, 2020

(30) Foreign Application Priority Data

Dec. 7, 2016   (AU) .................................. 2016905046

(51) Int. Cl.
*A61B 5/04*   (2006.01)
*A61B 5/00*   (2006.01)
(Continued)

(52) U.S. Cl.
CPC .......... *A61B 5/4362* (2013.01); *A61B 5/0002* (2013.01); *A61B 5/01* (2013.01);
(Continued)

(58) Field of Classification Search
CPC ..... A61B 5/4356; A61B 5/4362; A61B 5/391; A61B 5/344; A61B 5/6833; A61B 8/0866;
(Continued)

(56) References Cited

U.S. PATENT DOCUMENTS

2007/0191728 A1   8/2007   Shennib
2009/0062683 A1*  3/2009   Calderon ............... A61B 5/391
                                                            600/546
(Continued)

FOREIGN PATENT DOCUMENTS

GB     2121967 A        1/1984
WO     WO 2008/010215 A2  1/2008
(Continued)

OTHER PUBLICATIONS

International Search Report for Application No. PCT/AU2017/051346, dated Feb. 8, 2018 (7 pages).
(Continued)

*Primary Examiner* — Jon Eric C Morales
(74) *Attorney, Agent, or Firm* — Nixon Peabody LLP

(57) ABSTRACT

Apparatus and methods for monitoring pregnancy or labour are disclosed. In one embodiment the apparatus includes an electromyography (EMG) sensor having two or more EMG electrodes to monitor fetal or maternal activity during pregnancy or labour and one or more position sensors to monitor the relative positioning of the two or more EMG electrodes during the fetal or maternal activity. In one embodiment, the apparatus includes a monitoring device to be placed on a body and having a plurality of sensors integrated into the (Continued)

monitoring device, the plurality of sensors including at least: a first sensor configured to detect a first type of signal from the body indicative of a first type of fetal or maternal activity during pregnancy or labour; and a second sensor configured to detect a second type of signal from the body, different from the first type of signal, also indicative of the first type of fetal or maternal activity during pregnancy or labour.

57 Claims, 10 Drawing Sheets

(51) Int. Cl.
    *A61B 5/01*     (2006.01)
    *A61B 5/024*     (2006.01)
    *A61B 5/11*     (2006.01)
    *A61B 8/08*     (2006.01)
    *A61B 5/391*     (2021.01)

(52) U.S. Cl.
    CPC ............ *A61B 5/02411* (2013.01); *A61B 5/11* (2013.01); *A61B 5/1107* (2013.01); *A61B 5/391* (2021.01); *A61B 5/6823* (2013.01); *A61B 5/6833* (2013.01); *A61B 5/6843* (2013.01); *A61B 8/0866* (2013.01); *A61B 2562/0219* (2013.01); *A61B 2562/0261* (2013.01); *A61B 2562/164* (2013.01)

(58) Field of Classification Search
    CPC ..... A61B 8/02; A61B 2503/02; A61B 5/0011; A61B 5/389; A61B 5/4325; A61B 5/4343
    See application file for complete search history.

(56)     References Cited

U.S. PATENT DOCUMENTS

| | | |
|---|---|---|
| 2012/0065479 A1 | 3/2012 | Lahiji |
| 2015/0289822 A1 | 10/2015 | Dugan |
| 2016/0174840 A1 | 6/2016 | Udoh |
| 2016/0331299 A1 | 11/2016 | Cline |

FOREIGN PATENT DOCUMENTS

| | | | |
|---|---|---|---|
| WO | WO 2013/079073 A1 | 6/2013 |
| WO | WO 2015/020886 A1 | 2/2015 |

OTHER PUBLICATIONS

Written Opinion of International Searching Authority for Application No. PCT/AU2017/051346, dated Feb. 8, 2018 (16 pages).

\* cited by examiner

APPARATUS FOR MONITORING PREGNANCY OR LABOUR

CROSS-REFERENCE TO RELATED APPLICATIONS

The present application claims priority from PCT Application No. PCT/AU2017/051346, filed 7 Dec. 2017, which claims priority from Australian provisional patent application no. 2016905046, filed on 7 Dec. 2016, the content of both applications in their entirety which is incorporated herein by reference.

TECHNICAL FIELD

The present disclosure relates to an apparatus for monitoring pregnancy or labour.

BACKGROUND

Pregnancy and labour involve complex biological processes that are, to date, still poorly understood. The majority of women who undergo labour and subsequent delivery do so without the need for major medical intervention. However, there is a significant population of women who are unable, or choose not, to deliver naturally. This requires interventions such as caesarean section or operative vaginal delivery. Whilst medical interventions have improved both maternal and fetal outcomes over the last few decades, preventing death and traumatic injury, they are still associated with significant risks and complications.

Advancements in technology provide the potential to use less invasive and lower cost techniques to monitor the mechanics of labour. A better understanding of the mechanics of labour assists clinicians in identifying and assessing risks of poor pregnancy or labour progress at an earlier stage.

The majority of current labour monitoring systems use cardiotocography (CTG), more broadly known as electronic fetal monitoring (EFM). These monitoring systems use fetal heartrate and contraction frequency in order to predict if delivery is imminent as well as detecting any abnormalities or complications during pregnancy and labour. These systems tend to monitor fetal heart rate, using a Doppler ultrasound transducer or fetal electrocardiogram (fECG). They also monitor the presence of uterine contractions using either a separate device known as a tocodynanometer (TOCO), which is in effect a strain gauge that measures increased abdominal tension associated with contractions, or electromyography (EMG) to determine contraction presence. Such systems are however relatively cumbersome, uncomfortable and have difficulty recording in cases of movement or water immersion (shower, bath or similar). In addition the data provided by such devices, namely fetal heartrate and contraction frequency requires subjective interpretation known to increase rates of intervention. As a result of these factors combined patients are often restricted to a hospital setting where such systems are available and where trained clinicians are required to be present to operate and interpret readings from such systems. Further still, these systems also only allow for a limited assessment of activity during pregnancy and labour.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to an aspect of the present disclosure, there is provided an apparatus for monitoring pregnancy or labour, the apparatus comprising:
  a monitoring device to be placed on a body and comprising a plurality of sensors integrated into the monitoring device, the plurality of sensors including at least:
    a first sensor configured to detect a first type of signal from the body indicative of fetal or maternal activity during pregnancy or labour; and
    a second sensor configured to detect a second type of signal from the body, different from the first type of signal, indicative of fetal or maternal activity during pregnancy or labour.

In some embodiments, both the first and second types of signals may be indicative of body movement during pregnancy or labour. The body movement may be fetal movement and/or maternal movement.

The first sensor may be an electromyography sensor (EMG sensor) and the second sensor may be a temperature sensor. Alternatively, the first sensor may be an electromyography sensor and the second sensor may be an accelerometer. Alternatively still, the first sensor may be a temperature sensor and the second sensor may be an accelerometer.

In some embodiments, the fetal activity may comprise one or more of: fetal positioning, fetal movement and fetal heart rate. In some embodiments, the maternal activity comprise one or more of: muscle and uterine contractions, maternal positioning, maternal movement, maternal heart rate and maternal temperature.

In some embodiments, the type of fetal or maternal activity monitored by the different sensors may be the same.

According to an aspect of the present disclosure, there is provided an apparatus for monitoring pregnancy or labour, the apparatus comprising:
  a monitoring device to be placed on a body and comprising a plurality of sensors integrated into the monitoring device, the plurality of sensors including at least:
    a first sensor to detect a first type of signal from the body to provide an indication of a type of fetal or maternal activity during pregnancy or labour; and
    a second sensor to detect a second type of signal from the body, different from the first type of signal, to provide an indication of the same type of fetal or maternal activity as the first sensor.

In the preceding aspect, the first sensor may be an electromyography sensor and the second sensor may be a temperature sensor. Alternatively, the first sensor may be an electromyography sensor and the second sensor may be an accelerometer. Alternatively still, the first sensor may be a temperature sensor and the second sensor may be an accelerometer.

By providing different types of sensors that detect different signals from the body, but which are each configured to provide an indication of the same type of fetal or maternal activity, collection of data relating to pregnancy and/or labour can be more accurate and/or reliable. This may be particularly advantageous in an environment where fetal and/or maternal movement, interventions and the process of pregnancy or labour itself can otherwise result in missed or lost data. For example, if one sensor is interrupted due to non-contact, poor contact or other external influences, continuous uninterrupted monitoring of at least one type of signal may still be conducted due to the provision of the other sensor. In some instances, the monitoring device may be exposed to different conditions during a monitoring period, such as patient movement or exposure to water, which may result in one sensor being unsuitable for monitoring in a particular condition. Through the detection at least two different types of signals, that each provide an indication of the same type of fetal or maternal activity, loss or interruption of one sensor does not prevent the continual monitoring of that fetal or maternal activity as a useful signal can remain from the other sensor.

In some embodiments of apparatuses disclosed herein, the plurality of sensors may include a third sensor to detect a third type of signal from the body indicative of fetal or maternal activity during pregnancy or labour. The third sensor may be selected from the group comprising an accelerometer, a temperature sensor, an electromyography sensor and an ultrasound sensor.

In some embodiments, the plurality of sensors may include a fourth or further sensors selected from the group comprising an electromyography sensor and an ultrasound sensor.

In some embodiments, electromyography sensors can include electrohysterography sensors, i.e. electromyography sensors that are configured to monitor the uterus, for example.

In one embodiment, the first sensor is an electromyography sensor or an accelerometer and the second sensor is a temperature sensor, the first and second sensors both being configured to provide an indication of muscular or uterine contractions. In one embodiment, the first sensor is an electromyography sensor, the second sensor is a temperature sensor, and a third sensor is provided that is an accelerometer, the first, second and third sensors each being configured to provide an indication of muscular or uterine contractions.

The monitoring device may comprise a housing to house electronic components therein. The housing may be a sealed housing so as to prevent fluid ingress.

In some embodiments, the housing may comprise a top surface and a contoured bottom surface adapted for placement on the body. In one embodiment, the first sensor may be an electromyography sensor and the second sensor may be a temperature sensor, and wherein the plurality of sensors may further include an accelerometer. The electromyography sensor may comprise at least one electrical contact disposed on the bottom surface of the housing. The contact can be considered to provide at least partially an EMG electrode. The at least one electrical contact may be configured to receive and electrically couple to an EMG surface electrode, and may also be configured to protrude from the bottom surface such that the bottom surface is spaced from the body when the monitoring device is placed on the body. The temperature sensor may also be disposed on the bottom surface of the housing and the accelerometer may be disposed within the housing.

In some embodiments, the monitoring device may comprise a central portion and one or more flexible arm portions extending from the central portion. Each of the one or more flexible arm portions may be configured to be manipulable relative to the central portion so as to facilitate placement of the monitoring device on the body. In some embodiments, the monitoring device may comprise four flexible arm portions arranged in a cross-configuration. Each of the flexible arm portions may have an end portion with an opening, and an adhesive seal provided on the perimeter of the opening. The adhesive seal may be configured to adhere to the body so as to secure the monitoring device to the body and to form a water-tight barrier around the opening. In one embodiment, the first sensor may be an electromyography sensor and the second sensor may be a temperature sensor, and wherein the plurality of sensors may further include an accelerometer. The electromyography sensor may comprise a plurality of EMG electrodes. Both the adhesive seals and electrodes may, at least in part, be detachable from the apparatus to allow for replacement or cleaning as required by method of use.

In any aspects and embodiments disclosed herein, the electromyography sensor may comprise at least one EMG electrode disposed at a respective end portion. For example, at least one electrical contact can be disposed at a respective end portion and the at least one electrical contact may be configured to receive and electrically couple to an EMG surface electrode. The temperature sensor and the accelerometer may be disposed within the central portion. At least one of the arm portions may comprise a flex sensor.

The use of flex sensors may allow bending, flexing, stretching, contraction, deformation and/or other types of movement (e.g. changes in shape and/or dimensions) of the arm portions to be detected. This movement may arise due to body movement, such as abdominal movement caused by contractions and/or fetal movement. The body movement may result in relative movement of EMG electrodes of the electromyography sensor. Thus, the one or more flex sensors may allow for monitoring of the relative position of two or more of the EMG electrodes. In addition or as an alternative to flex sensors, e.g. for the purpose of monitoring the relative position of the two or more EMG electrodes, one or more other types of sensors, such as stretch sensors, may be used, which other sensors can also allow changes in shape and/or dimensions of portions of the apparatus structure to be detected.

According to an aspect of the present disclosure, there is provided an apparatus for monitoring pregnancy or labour, the apparatus comprising:

a monitoring device to be placed on a body, the monitoring device comprising:

an electromyography sensor comprising two or more EMG electrodes to monitor fetal or maternal activity during pregnancy or labour; and one or more position sensors to monitor the relative positioning of the two or more EMG electrodes during the fetal or maternal activity.

The one or more position sensors may be flex sensors or other types of sensors, such as stretch sensors, that can monitor bending, flexing, stretching, contraction, deformation and/or other types of changes in the structure of the monitoring device. When a flex or stretch sensor is used, for example, it may monitor the changes based on changes in resistance or capacitive of a component comprised in the sensor, for example. The two or more EMG electrodes may be located on respective arm portions and the position sensors may monitor movement, e.g. bending or flexing, of the arm portions. The position sensors may monitor changes in relative position of the two or more EMG electrodes during fetal or maternal activity. A change in the relative position of the two or more EMG electrodes, when the EMG electrodes are fixed to the abdomen, for example, can be indicative of deformation of the body, e.g. of the abdomen, during the fetal or maternal activity. The monitoring of the relative positioning of the two or more EMG electrodes during the fetal or maternal activity may comprise determining a distance or change in distance between the two or more EMG electrodes.

By monitoring the position of the two or more EMG electrodes during the fetal or maternal activity, the EMG signals obtained from those electrodes can be interpreted in light of their relative positioning, enabling a more holistic analysis of the generated data. For example, it can enable EMG signal changes to be correlated with a distortion in the body adjacent the monitoring device, the distortion occurring as a result of contractions or otherwise.

The monitoring of movement may be conducted with reference to a reference location of the monitoring device. The reference location may be at a central location of the monitoring device. The reference location may be at the central portion of the monitoring device from which the arm portions may extend, for example.

The EMG electrodes may be fixed to the body, e.g. adhered to the body in accordance with techniques described above. The central portion may also be fixed to the body, e.g., adhered to the body. Thus the electrodes and the reference location may retain respective fixed positions relative to the body. Portions of the monitoring device between the reference location and the electrodes may be spaced from the body. For example, the arm portions may bridge the space between the central portion and the electrode contact locations without little or no contact with the body, ensuring that the monitoring device does not significantly impede natural movement, e.g. deformation, of the body. The arm portions may be arched or otherwise raised over the body and may be flexible, as discussed above.

The relative positioning of the two or more EMG electrodes may be determined based on a trigonometrical calculation. The length between a first one of the EMG electrodes and the reference location can provide a first side of a notional triangle, the length between a second one of the EMG electrodes and the reference location can provide a second side of the notional triangle, and the length between the two electrodes can provide a third side of the notional triangle. The angle between the first and second sides may be a substantially fixed angle, e.g. if the flexible arm portions are only flexible in a length direction, and/or may be determined based on monitoring of flex of the arm portions, e.g. by the flex or stretch sensors, in two or more dimensions. The third side of the notional triangle, and thus the distance between the two electrodes, may be calculated from knowledge of the lengths of the first and second sides and their relative angle. Nevertheless, other types of calculations may be made to monitoring the electrode positioning based on data from the position sensors.

In any of the above aspects and embodiments, the monitoring device may be adapted to be placed on the abdomen. The monitoring device may be located over the fundus of the uterus, for example. It has been found, for example, that location of the monitoring device, and thus the plurality of sensors, over the fundus, allows different types of sensors to be used by the monitoring device to monitor the same types of fetal or maternal activity. For example, it has been found that in addition to placing an electromyography sensor or an accelerometer (e.g. as a first sensor) at the fundus to monitor activity such as muscular or uterine contractions, a temperature sensor can be used as a second sensor to reliably monitor the same activity, such as the same muscular or uterine contractions, when at the fundus.

The apparatus may further comprise a user interface coupled to the monitoring device, the user interface comprising a display for displaying information derived from the signals detected by the plurality of sensors. The user interface may comprise one or more of a desktop computer, a laptop computer, a smartphone, a personal digital assistant, a watch, a data collection band and other devices of the like configured to display the information. Additionally or alternatively, the apparatus may comprise a user interface integrated into the monitoring device. For example, the user interface may be an on-board indicator. The user interface may provide an indication of the type of data being collected by the monitoring device and/or indication about the attachment status of the device to the body, power levels or otherwise.

The apparatus may be configured to process the signals received from each of the plurality of sensors so that they each present a similar indication, on the user interface, for the same type of fetal or maternal activity. The signals may be presented as time-plots on a display and amplitudes of the plots may be such that a corresponding type of fetal or maternal activity is presented in the plots in a similar manner. For example, the signals may be processed so that, when a uterine contraction takes place, a consequential change in amplitude of the plot for the first signal may be the same or similar to the change in amplitude of the plot for the second or further signals. The change in amplitude of the plots may have the same direction. The change in amplitude of the plots may be configured to be within a factor of 4, 3, 2 or 1.5, for example. The scale of the plots displayed by the user interface may be selected or programmed to provide this effect.

The monitoring device may further comprise at least one reference sensor adapted to be placed on the body in a location spaced from the monitoring device, where fetal or maternal activity will be absent, so as to provide a reference to the plurality of sensors. In some embodiments, the at least one reference sensor may be adapted to be placed at the ribs. In other embodiments, the at least one reference sensor may be adapted to be placed at the hip or sternum. The at least one reference sensor may comprise one or more of an electromyography sensor, a temperature sensor, an accelerometer, and an ultrasound sensor, for example. The at least one reference sensor may be positioned externally to the housing and may be movable relative to the housing. The at least one reference sensor may be connected to the housing via a wire that retains a physical and/or electrical connection between the reference sensor and the other components of the monitoring device, or may be wirelessly connected.

The apparatus may further comprise one or more roving sensors independent of the monitoring device. The one or more roving sensors may comprise a fetal heart rate monitor and/or a maternal heart rate monitor, for example. In addition, or alternatively, the one or more roving sensors may comprise an electromyography sensor.

In any of the aspects described herein, the apparatus may be adapted for use in a clinical setting such as a hospital, birth centre or doctor's surgery. Additionally or alternatively, the apparatus may be adapted for use in a non-clinical setting such as a home. The apparatus may designed as 'point-of-care' apparatus, whether for home use or otherwise. The apparatus may provide a means for remote monitoring of a patient. In this regard, signals and/or other data received by the apparatus may be transmitted, e.g. by the monitoring device, to a remotely located user interface for observation or analysis by a third party. The apparatus may be provide a means for monitoring a patient during pregnancy and/or during labour.

According to another aspect of the present disclosure, there is provided a method comprising:

placing a monitoring device on a body, the monitoring device comprising a plurality of sensors integrated therein;

detecting a first type of signal from the body via a first sensor of the plurality of sensors; and detecting a second type of signal from the body, different from the first type of signal, via a second sensor of the plurality of sensors, wherein the first and second types of signals are indicative of fetal or maternal activity during pregnancy or labour.

According to another aspect of the present disclosure, there is provided a method comprising:

placing a monitoring device on a body, the monitoring device comprising a plurality of sensors integrated therein;

detecting a first type of signal from the body via a first sensor of the plurality of sensors; and detecting a second type of signal from the body, different from the first type of signal, via a second sensor of the plurality of sensors, and using the detected signals from the first sensor to monitor a type of fetal or maternal activity; and using the detected signals from the second sensor to monitor the same type of fetal or maternal activity as monitored using the first sensor.

The method may comprise detecting a third type of signal from the body via a third sensor of the plurality of sensors. The third type of signal may be indicative of fetal or maternal activity during pregnancy or labour.

The method may further comprise detecting a signal from a fourth or further sensors selected from the group comprising an electromyography sensor and an ultrasound sensor, for example.

The first sensor may be an electromyography sensor and the second sensor may be a temperature sensor. Alternatively, the first sensor may be an electromyography sensor and the second sensor may be an accelerometer. Alternatively still, the first sensor may be a temperature sensor and the second sensor may be an accelerometer.

In one embodiment, the first sensor is an electromyography sensor or an accelerometer and the second sensor is a temperature sensor, the first and second sensors both being used to monitor muscular or uterine contractions. In one embodiment, the first sensor is an electromyography sensor, the second sensor is a temperature sensor, and a third sensor is provided that is an accelerometer, the first, second and third sensors each being used to monitor muscular or uterine contractions.

By providing different types of sensors that detect different signals from the body, but which are each used to monitor the same type of fetal or maternal activity, collection of data relating to pregnancy and/or labour can be more accurate and/or reliable for reasons as discussed above with respect to preceding aspects.

The method may further comprise displaying information based on the types of signals obtained from the plurality of sensors. Displaying the information may comprise presenting the signals as time-correlated plots on a display. The displaying may be such that the amplitudes of the plots may change, for a corresponding type of fetal or maternal activity, in a similar manner. For example, the displaying may be such that, when a uterine contraction takes place, a consequential change in amplitude of the plot for the first signal may be the same or similar to the consequential change in amplitude of the plot for the second or further signals. The change in amplitude of the plots may have the same direction. The change in amplitude of the plots may be within a factor of 4, 3, 2 or 1.5, for example.

According to another aspect of the present disclosure, there is provided a method of monitoring pregnancy or labour, the method comprising:

placing a monitoring device on a body, the monitoring device comprising an electromyography sensor comprising two or more EMG electrodes and one or more position sensors;

monitoring fetal or maternal activity during pregnancy or labour using the EMG electrodes of the electromyography sensor; and monitoring the relative positioning of the two or more EMG electrodes during the fetal or maternal activity using the one or more position sensors.

In any of the aspects described herein, the placing of the monitoring device on the body may comprise placing the monitoring device on the fundus of the abdomen.

BRIEF DESCRIPTION OF DRAWINGS

Embodiments of the invention will now be described, by way of example only, with reference to the accompanying drawings, in which.

DESCRIPTION OF EMBODIMENTS

Figure 1:
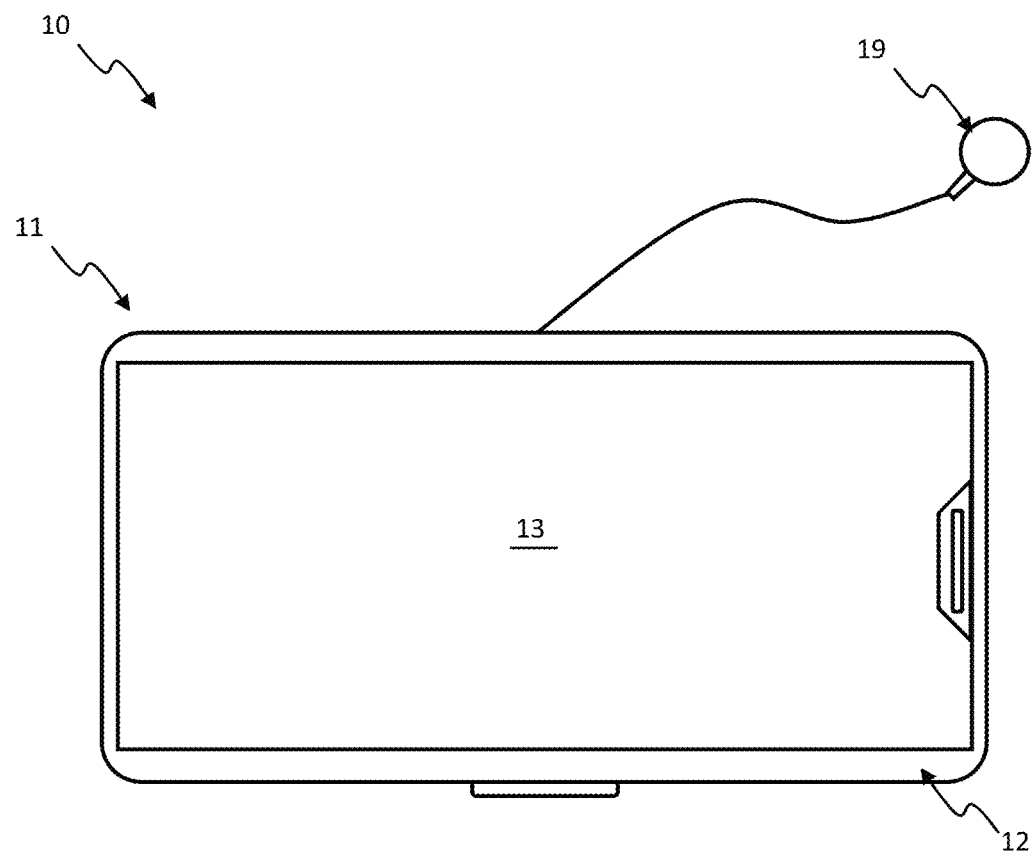
FIG. 1 is a top view of an apparatus according to an embodiment of the present disclosure.
Figure 2:
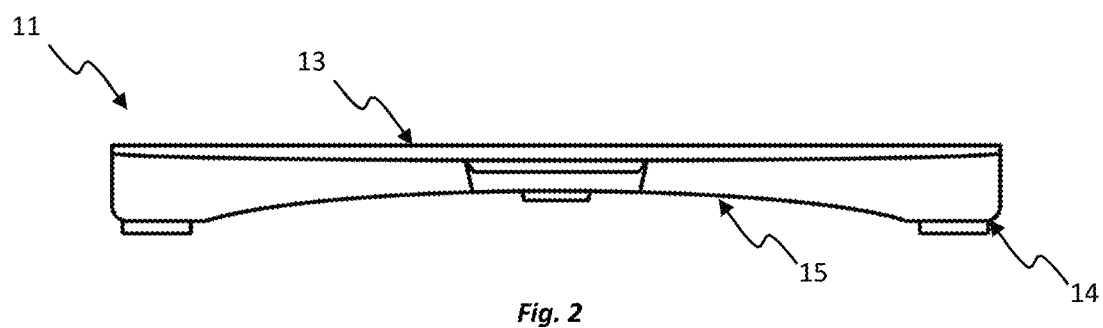
FIG. 2 is a front view of the apparatus of FIG. 1.

FIGS. 1, 2, 3a and 3b show an apparatus 10 for monitoring pregnancy or labour according to an embodiment of the present disclosure. The apparatus 10 comprises a monitoring device 11 adapted to be placed on a body. The monitoring device 11 has a housing 12 which houses electronic components of the monitoring device 11. The housing 12 has a top surface 13 and a bottom surface 14. As best seen in FIG. 2, the bottom surface 14 has a contoured portion 15 corresponding substantially to a curvature of the maternal abdomen. The housing 12 is sealed so as to prevent fluid ingress.

The monitoring device 11 further comprises a plurality of sensors integrated into the monitoring device 11. The plurality of sensors include at least a first sensor configured to detect a first type of signal from the body that is indicative of fetal or maternal activity during pregnancy or labour, and a second sensor configured to detect a second type of signal from the body, different from the first type of signal, that is also indicative of fetal or maternal activity during pregnancy or labour. The type of fetal or maternal activity monitored by the different sensors can be the same. Detecting different types of signals can allow for accurate collection of data in an environment where fetal and/or maternal movement, interventions and the process of pregnancy or labour itself can otherwise result in missed or lost data. For example, if one sensor is interrupted due to non-contact, poor contact or other external influences, continuous uninterrupted monitoring of at least one type of signal may still be conducted due to the provision of the other sensor. The present disclosure recognises that the monitoring device 11 may also be exposed to different conditions during a monitoring period, such as patient movement or exposure to water, which may result in one sensor being unsuitable for monitoring in a particular condition. However, as the monitoring device 11 detects at least two different types of signals, loss or interruption of one sensor does not prevent the continual monitoring of fetal or maternal activity, since detection of a useful signal remains from the other sensor.

In some embodiments, the first and second types of signals are both indicative of body movement during pregnancy or labour. The body movement may be fetal movement and/or maternal movement, for example. Fetal activity may also comprise for example fetal positioning and/or fetal heart rate. Maternal activity may also comprise for example muscle and uterine contractions, maternal positioning, maternal heart rate and/or maternal temperature.

The first and second sensors may be any combination of two different sensors selected from the group comprising an electromyography (EMG) sensor for detecting uterine contractions, a temperature sensor for detecting fetal and/or maternal body temperature, and an accelerometer for detecting fetal and/or maternal positioning and movement. For example, the first sensor may be an EMG sensor and the second sensor may be a temperature sensor. In another alternate example, the first sensor may be an EMG sensor and the second sensor may be an accelerometer. In yet another alternate example, the first sensor may be a temperature sensor and the second sensor may be an accelerometer.

The monitoring device 11 may also comprise a third sensor to detect a third type of signal from the body that is indicative of fetal or maternal activity during pregnancy or labour. In some embodiments, the third type of signal may be the same as the first type of signal or the second type of signal. In other embodiments, the third type of signal may be different from the first and second types of signals. The third sensor may be selected from the group comprising an accelerometer, a temperature sensor, an EMG sensor and an ultrasound sensor, for example.

The monitoring device 11 may also comprise yet further sensors, e.g., any combination of four or more sensors, with at least two sensors being configured to detect a different type of signal. The further sensors may be selected from the group comprising an accelerometer, a temperature sensor, an EMG sensor and an ultrasound sensor, for example.

Figure 3A:
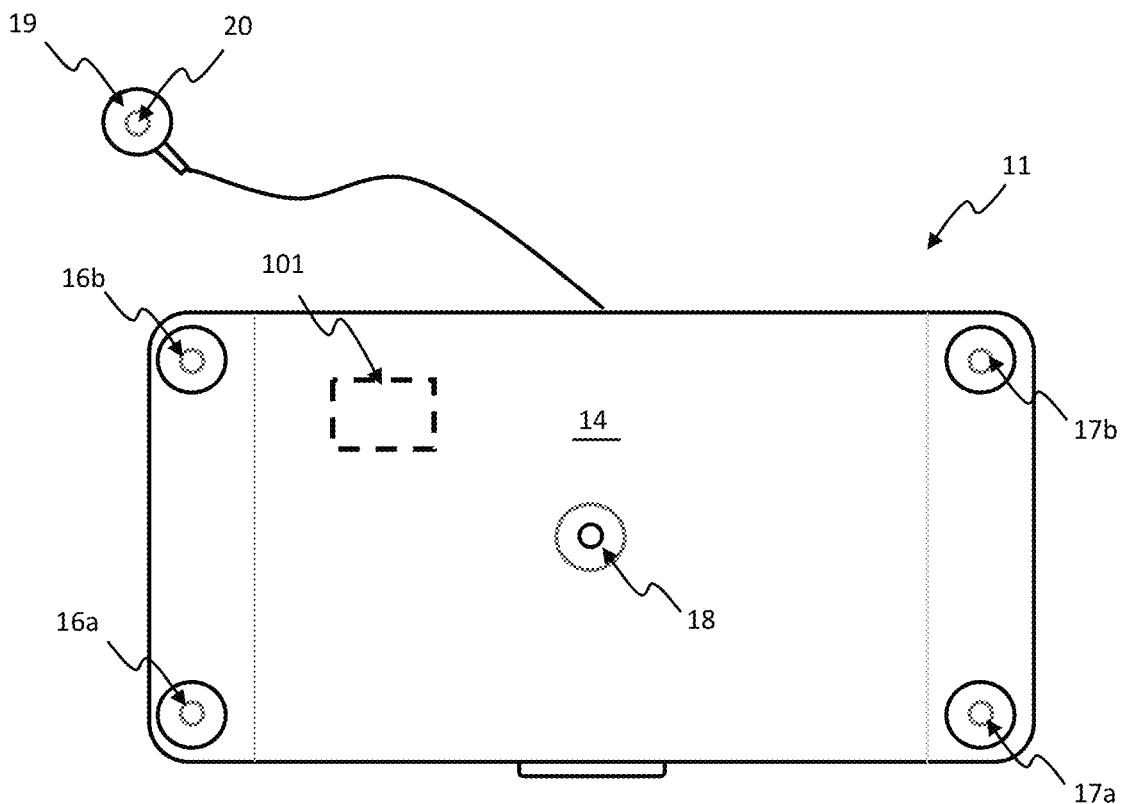
FIG. 3a is a bottom view of the apparatus of FIG. 1.

Referring to the embodiment depicted in FIG. 3*a*, the monitoring device 11 comprises four sensors, three of which are configured to detect different types of signals. In particular, the monitoring device 11 includes two EMG sensors 16, 17, a temperature sensor 18 and an accelerometer 101, all integrated into the monitoring device 11. One of the three different sensors, such as one of the EMG sensors 16, 17, can be considered to provide a first sensor that is configured to detect a first type of signal from the body indicative of fetal or maternal activity during pregnancy or labour. Another of the sensors, such as the temperature sensor 18 or accelerometer 101, can be considered to provide a second sensor that is configured to detect a second type of signal from the body, different from the first type of signal, but again indicative of fetal or maternal activity during pregnancy or labour.

Figure 3B:
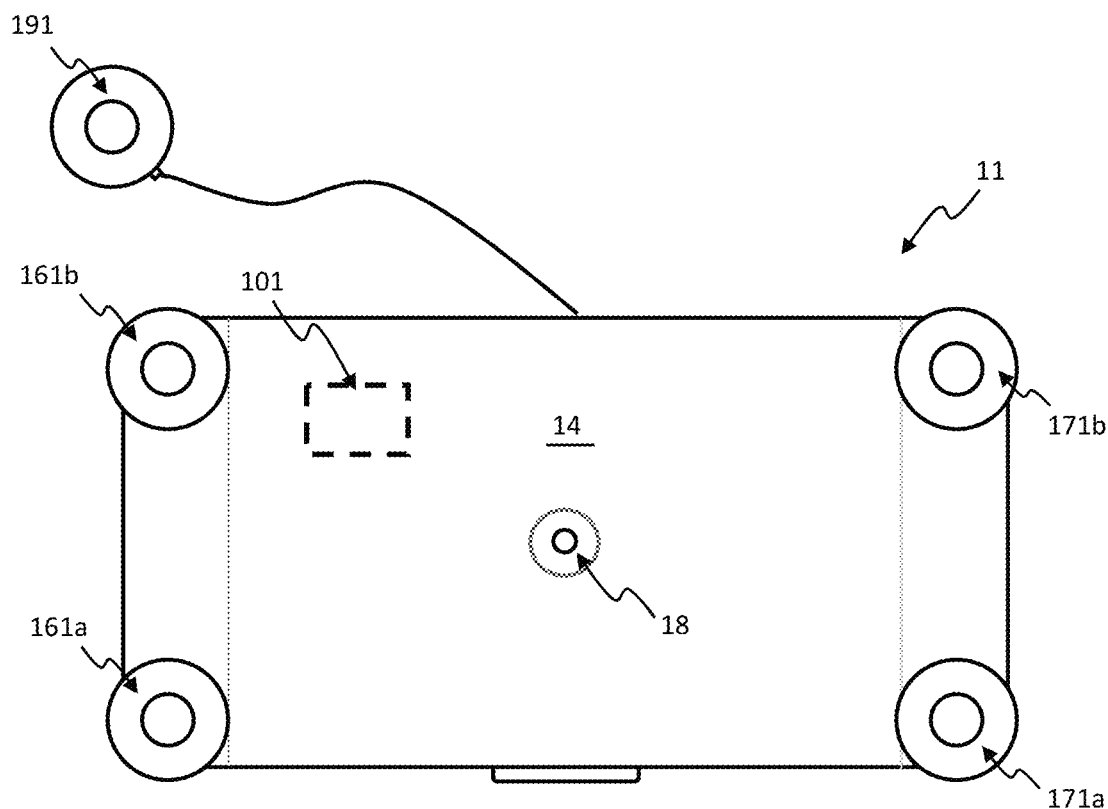
FIG. 3b is a bottom view of the apparatus of FIG. 1, showing EMG surface electrodes of the apparatus.

Each of the EMG sensors 16, 17 includes a pair of contact points 16*a*, 16*b*, 17*a*, 17*b* disposed on the bottom surface 14 of the housing 12. The contact points 16*a*, 16*b*, 17*a*, 17*b* protrude from the bottom surface 14. The protrusion is such that the bottom surface 14 is spaced from the body when the monitoring device 11 is placed on the body, which can allow for ventilation or aeration between the body and the monitoring device 11, improving patient comfort. The contact points 16*a*, 16*b*, 17*a*, 17*b* can be considered to provide EMG electrodes. However, in this embodiment, the contact points 16*a*, 16*b*, 17*a*, 17*b* are also each configured to receive and electrically couple to a respective removable EMG surface electrode 161*a*, 161*b*, 171*a*, 171*b* as shown in FIG. 3*b*. The EMG surface electrodes 161*a*, 161*b*, 171*a*, 171*b* are configured to contact the skin. The EMG sensors 16, 17 through electrical contact with the skin are configured to detect changes in potential differences (voltage) caused by uterine contractions or other fetal and/or maternal activity.

The accelerometer 101 is disposed within the housing 12 and is configured to monitor maternal and/or fetal movement. The temperature sensor 18 is disposed on the bottom surface 14 of the housing 12 and is configured to track fluctuations in maternal temperature. For example, use of a temperature sensor 18 may aid in the identification of fever due to infection. In addition or alternatively, the temperature sensor 16 may also be used to detect the onset and/or occurrence of uterine contractions. In this regard, the present disclosure recognises that fluctuations in maternal temperature, specifically a change in body temperature from baseline temperatures, can be synonymous with the onset or occurrence of uterine contractions (as discussed below).

Figure 4A:
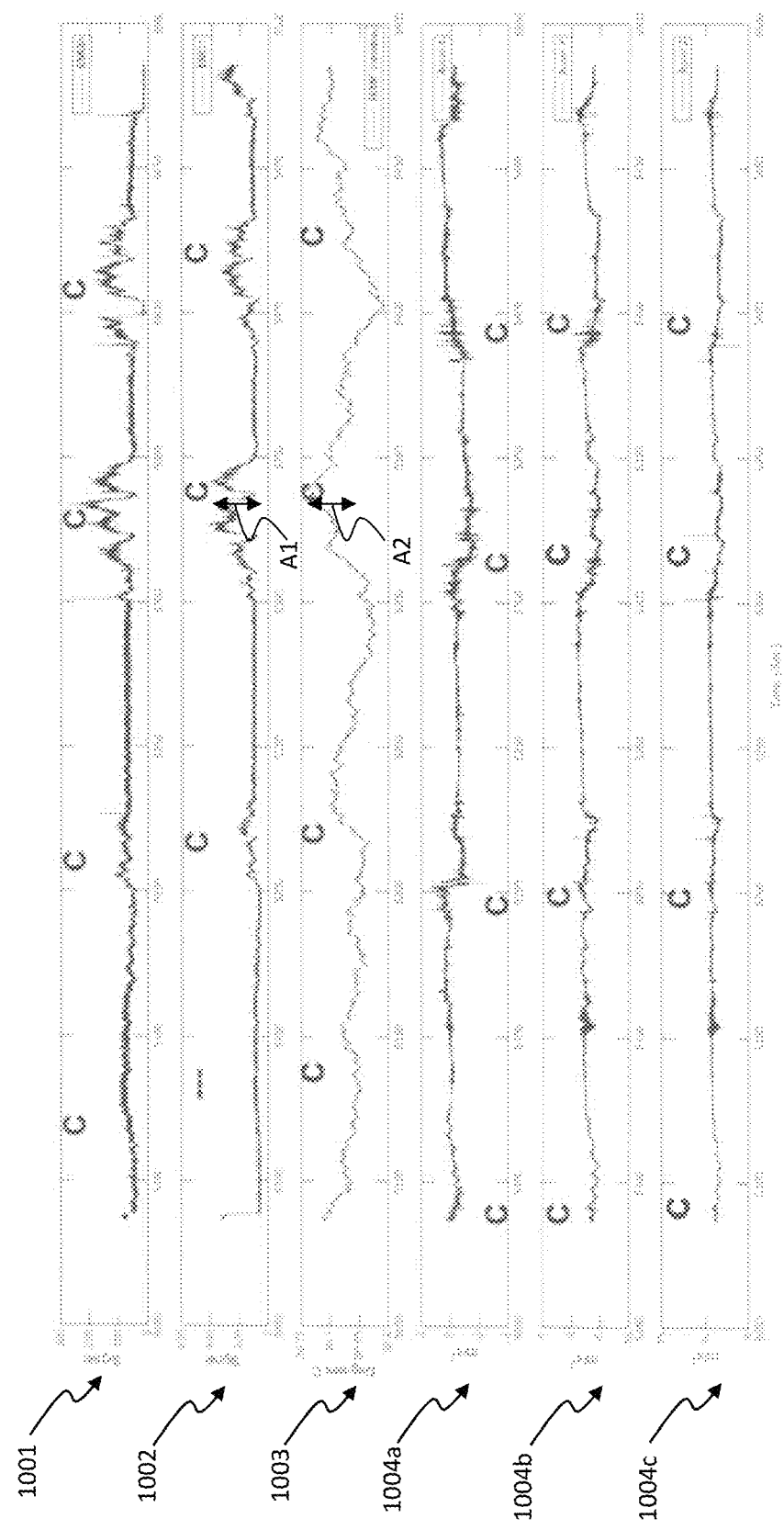
FIG. 4a is a plot showing a pattern of signals over a period of uterine contractions detected using the apparatus of FIG. 1.
Figure 4B:
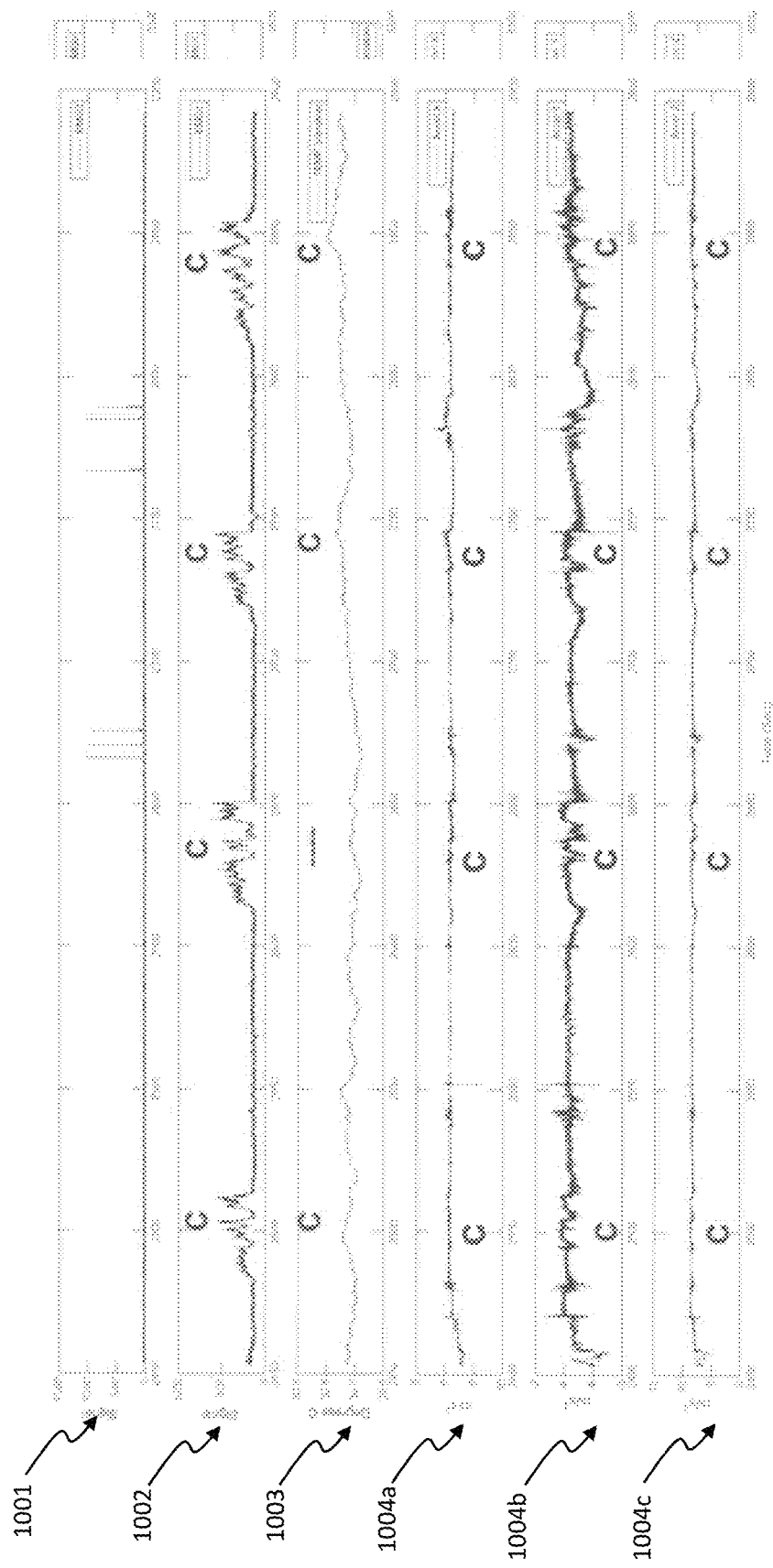
FIG. 4b is a plot showing a pattern of signals over a period of uterine contractions detected using the apparatus of FIG. 1, with poor or lost connection of one electromyography (EMG) sensor.
Figure 4C:
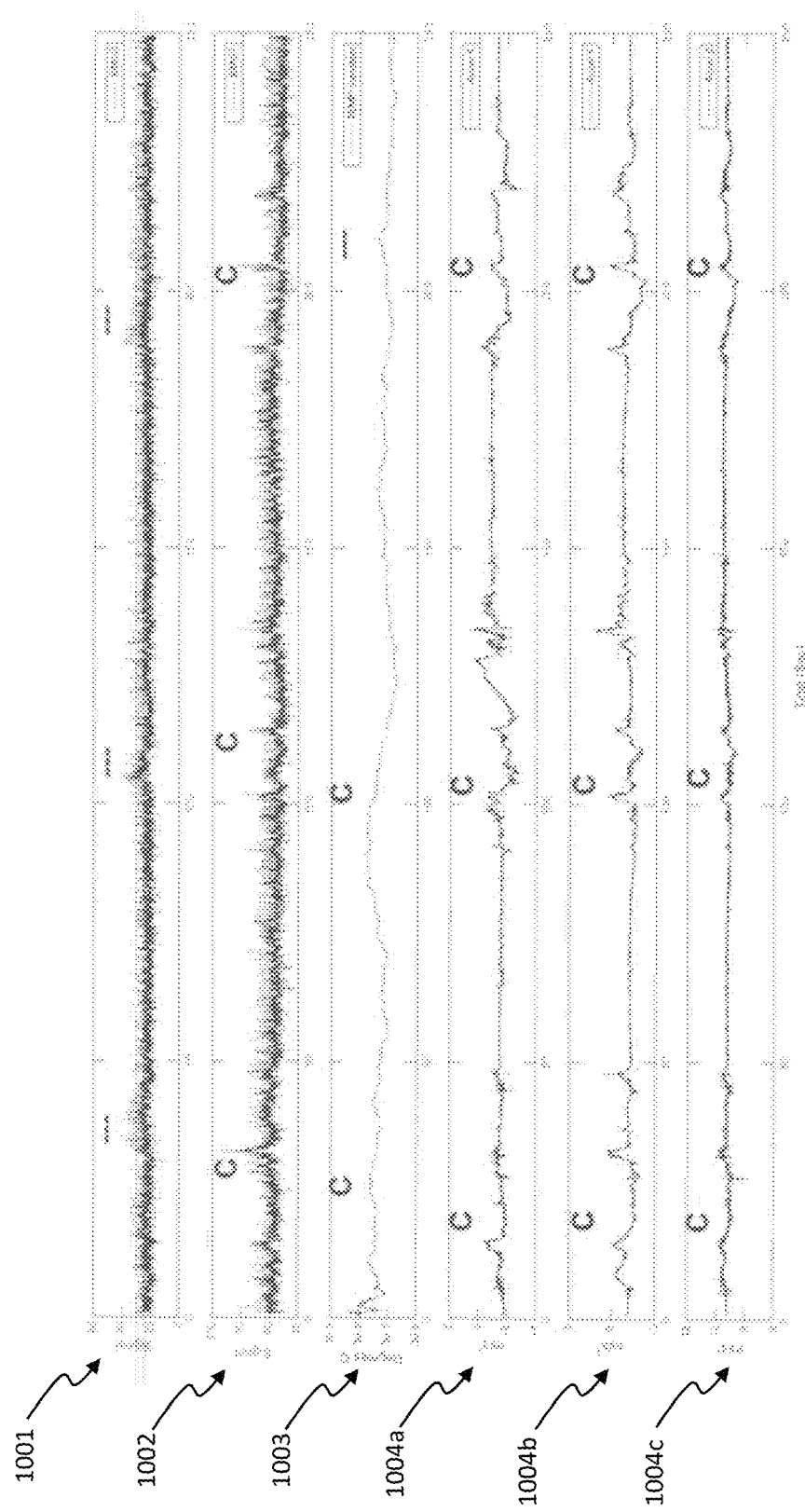
FIG. 4c is a plot showing a pattern of signals over a period of uterine contractions detected using the apparatus of FIG. 1, with noise interruption to both electromyography sensors.

FIGS. 4*a* to 4*c* show examples of signals recorded over a period of time of patients undergoing contractions using the monitoring device 11 and as presented by a user interface. The plots show two signals 1001, 1002 detected from the two EMG sensors 16, 17, a signal 1003 detected from the temperature sensor 18 and three signals 1004*a*, 1004*b*, 1004*c* detected along three different axes from the accelerometer 101, of the monitoring device 11. The signals 1001-1004*c* are time-correlated in the plots.

FIG. 4*a* shows that a repeated pattern of contractions (indicated by the letter 'C') can be identified across all three sensor types. It can be recognised that fluctuations in maternal temperature (i.e. a change in body temperature from baseline temperatures) can also be attributed to uterine contractions, for example. In this example, rises in body temperature can be attributed to uterine contractions, for example, albeit in alternative examples, other patterns of temperature change may also be indicative of uterine contractions. Therefore, as discussed above, the plurality of sensors can provide for continual monitoring of at least one type of signal indicative of fetal or maternal activity, such as uterine contractions, thus ensuring that no critical data may be missed or lost during a monitoring period.

So that the different plots of the signals 1001-1004*c* can readily provide a user with an indication regarding the same type of fetal or maternal activity, the scale of the plots is adjusted by the user interface so that, when a uterine contraction takes place, a consequential change in amplitude of the plot for the different signals 1001-1004*c* is the same or similar. For example, with reference to FIG. 4*a*, the amplitude A1 for a contraction as identifiable in the EMG signal plot 1001b is the same or similar to the amplitude A2 for a contraction as identifiable in the temperature signal plot 1002.

The present disclosure recognises that the patient may not necessarily be confined to a hospital setting for monitoring of pregnancy or labour to occur. Monitoring may be required when the patient is moving (e.g. walking, turning in bed, etc.) or when the patient is in a shower or bath during pregnancy or labour, for example. The plurality of sensors of the monitoring device 11 may therefore be exposed to different conditions during a monitoring period. Such conditions may result in one or more types of signals detected by the plurality of sensors being lost or interrupted during a monitoring period. However, as the monitoring device 11 detects at least two different types of signals, loss or interruption of one type of signal does not prevent the continual monitoring of fetal or maternal activity, since useful signals remain from the other sensors. This is evidenced by FIG. 4b, for example, which shows that poor or lost connection of one EMG sensor, resulting in a substantially absent signal 1001, does not prevent the continual monitoring of fetal or maternal activity, since useful signals remain from the other sensors. Similarly, as can be seen in FIG. 4c, continual monitoring of fetal or maternal activity is not missed or lost even when signals 1001, 1002 from both EMG sensors are interrupted by noise, due to exposure of the EMG sensors to water, for example.

Referring again to FIGS. 1, 3a and 3b, the monitoring device 11 may also comprise at least one reference sensor 19 adapted to be placed on the body in a location spaced from the monitoring device 11, where fetal or maternal activity will be absent, so as to provide a reference to the plurality of sensors and enable filtering of the signals occurring due to maternal or fetal activity from signals derived from other sources, such as gross body movement (e.g. walking, turning in bed, etc.) or normal temperature fluctuations. In some embodiments, the at least one reference sensor 19 may be placed at the ribs. It will be appreciated however that the at least one reference sensor 19 may be placed elsewhere on the body, such as at the hip or sternum, for example, or a reference sensor may be excluded in other embodiments.

In some embodiments, the at least one reference sensor 19 may comprise one or more of an EMG sensor, a temperature sensor, an accelerometer and an ultrasound sensor. In the embodiment depicted in FIGS. 1, 3a and 3b, the reference sensor 19 may be an EMG sensor of the type described above for providing a reference to the EMG readings from the EMG sensors 16, 17 of the monitoring device 11. The reference sensor can be wired to the monitoring device 11 or may be a physically separate wireless unit, enabling it to be located on a more separate part of the body. In this particular embodiment, the reference sensor 19 may have a contact point 20 adapted to receive and electrically couple to a removable EMG surface reference electrode 191 as shown in FIG. 3b. In this example, filtering of the signals occurring due to maternal or fetal activity may be achieved by subtracting the signal derived from the reference sensor 19 from the signal derived from any of the EMG sensors 16, 17 of the monitoring device 11.

Figure 5:
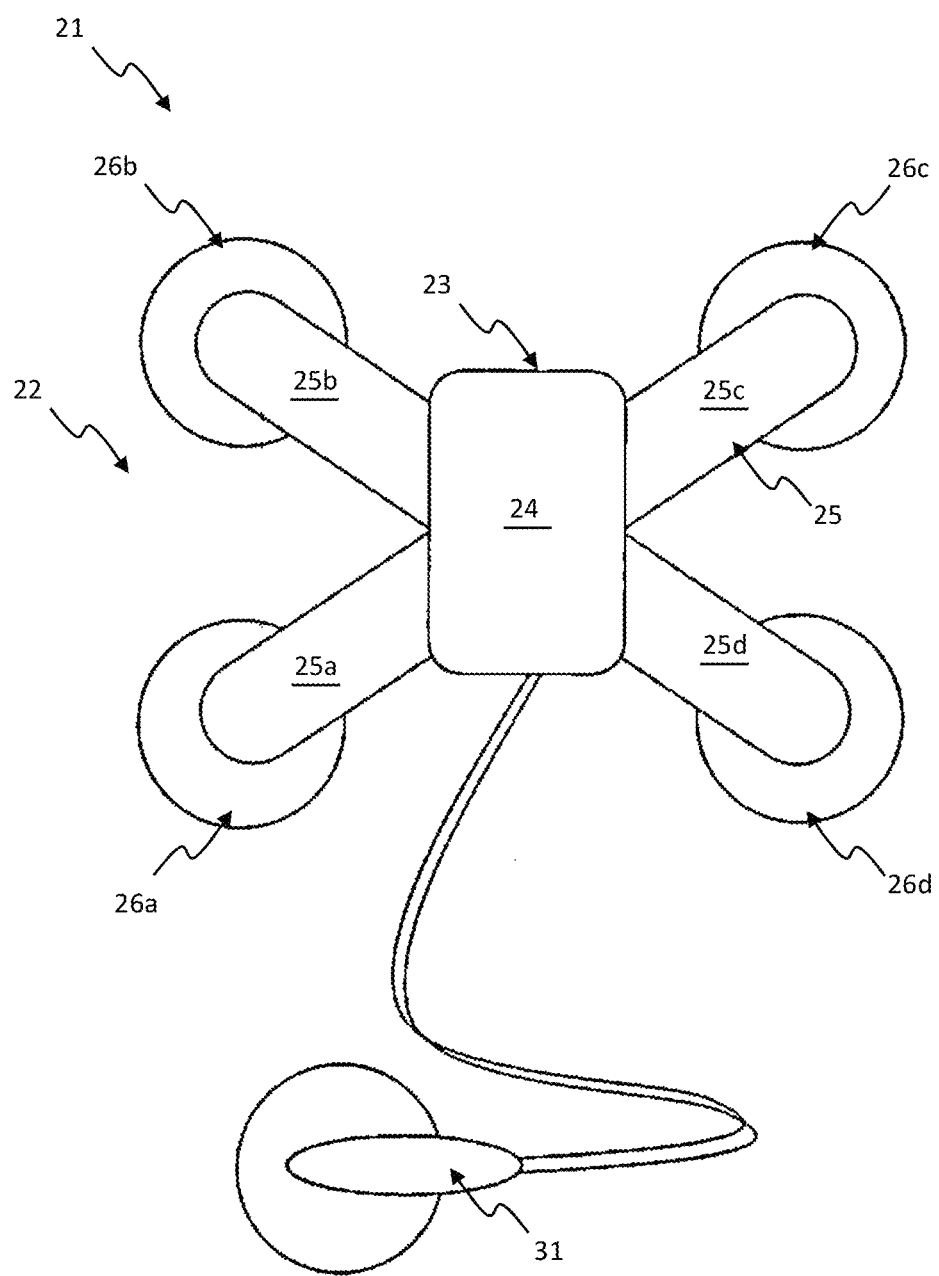
FIG. 5 is a top view of an apparatus according to another embodiment of the present disclosure.
Figure 6A:
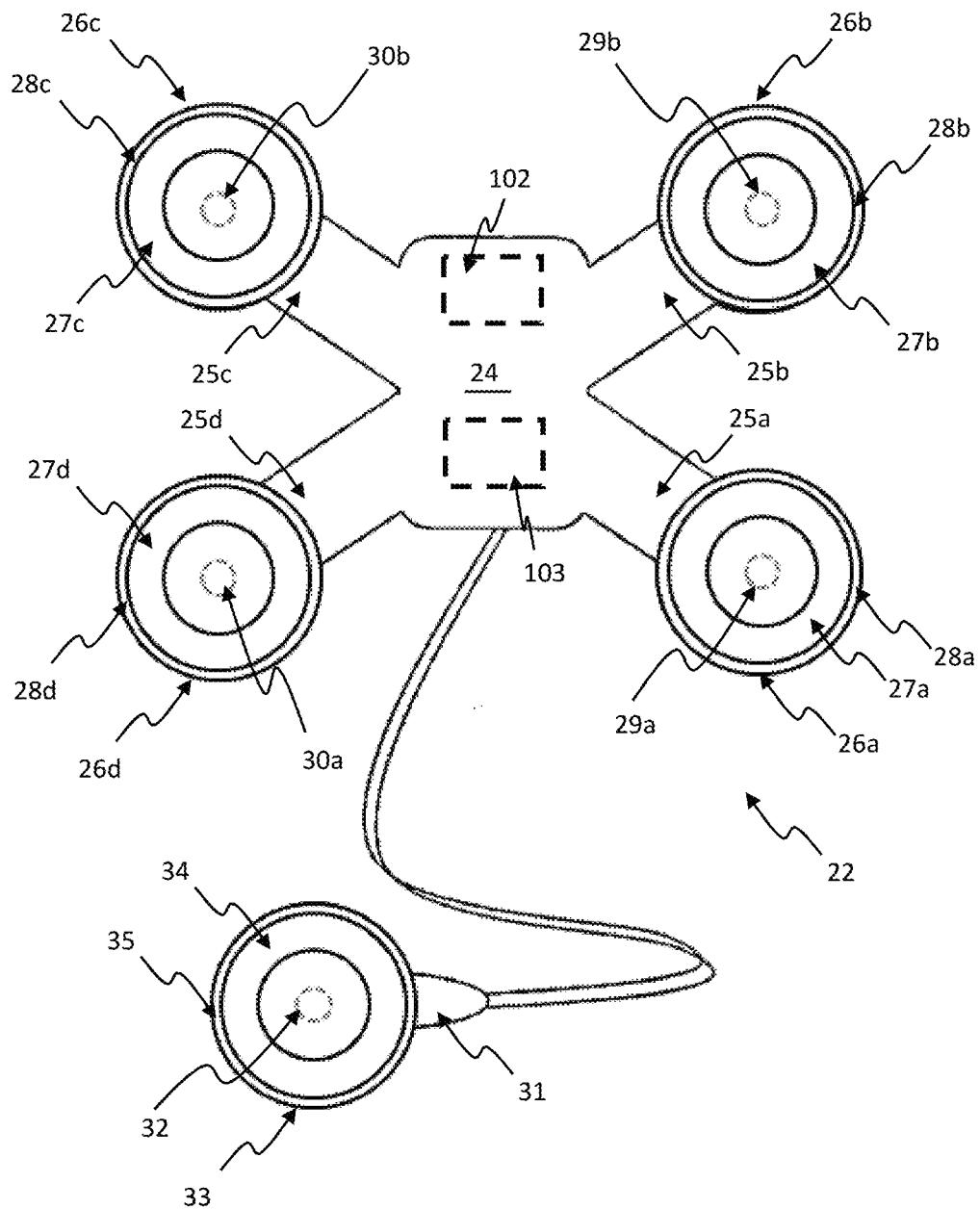
FIG. 6a is a bottom view of the apparatus of FIG. 5.
Figure 6B:
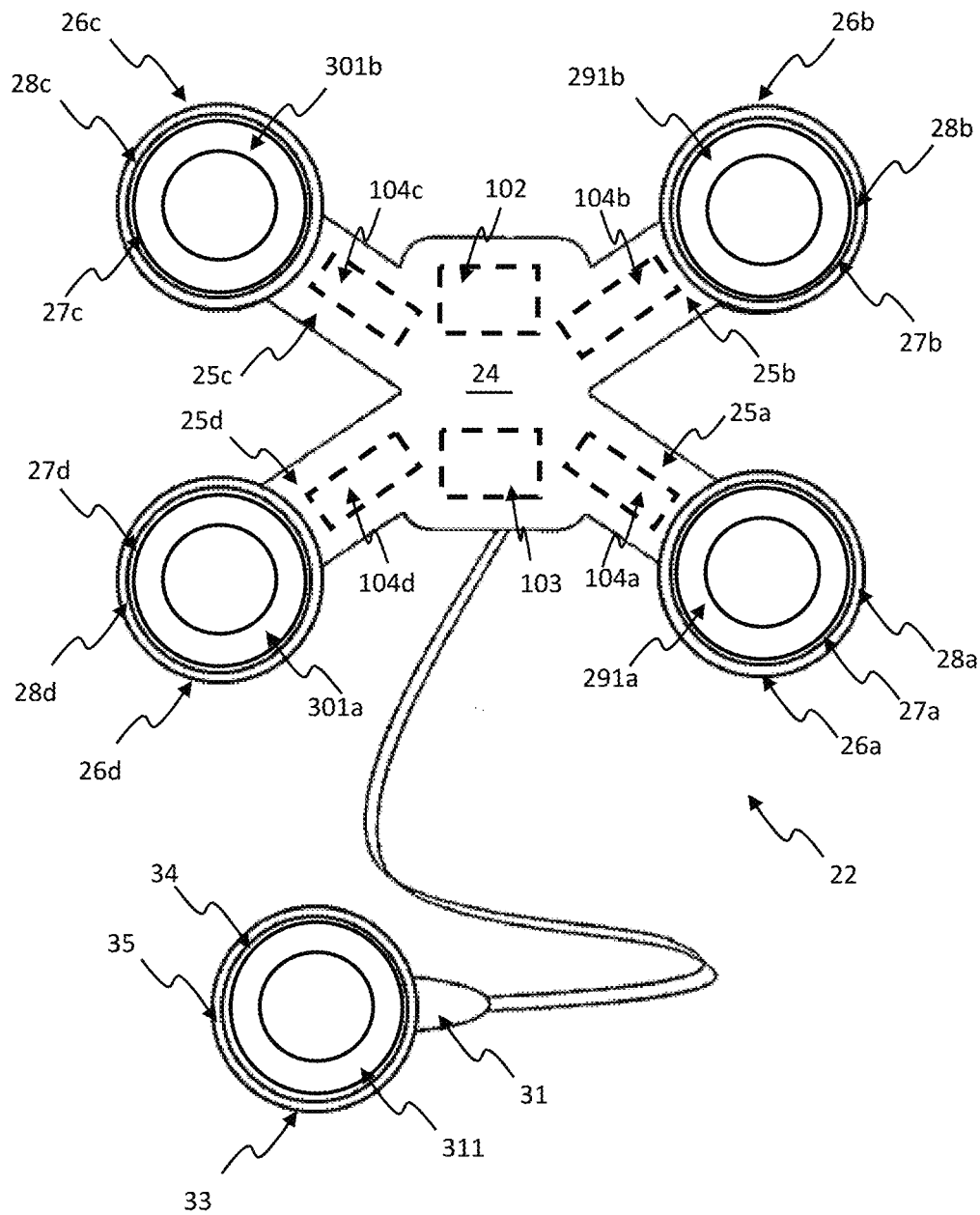
FIG. 6b is a bottom view of the apparatus of FIG. 5, showing EMG surface electrodes of the apparatus.

FIGS. 5, 6a and 6b show an apparatus 21 for monitoring pregnancy or labour according to another embodiment of the present disclosure. The apparatus 21 comprises a monitoring device 22 adapted to be placed on the body. The monitoring device 22 has a central portion 24 and one or more flexible arm portions 25 connected to the central portion 24. The one or more flexible arm portions 25 are each configured to be independently manipulable relative to the central portion 24 so as to facilitate placement of the monitoring device 22 on the body regardless of the curvature of the maternal abdomen and bend and flex in order to conform to any presenting deformation and movements of the body while being worn. The monitoring device 22 also has a housing 23 at the central portion which houses electronic components of the monitoring device 22. The housing 23 is sealed to prevent fluid ingress, thus preventing exposure of electronic components of the monitoring device 22 to potentially harmful environmental factors, such as water and dust, for example.

In the embodiment depicted in FIGS. 5 and 6, the monitoring device 22 has four flexible arm portions 25a, 25b, 25c, 25d extending outwardly from the central portion 24 so as to be arranged in a cross-configuration. The flexible arm portions 25a, 25b, 25c, 25d have end portions 26a, 26b, 26c, 26d with openings 27a, 27b, 27c, 27d. Adhesive seals 28a, 28b, 28c, 28d, which may be detachable, are provided on the perimeter of the openings 27a, 27b, 27c, 27d and are each configured to adhere to the body so as to secure the monitoring device 22 to the body and to form a water-tight barrier around the openings 27a, 27b, 27c, 27d.

The monitoring device 22 also comprises a plurality of sensors integrated into the monitoring device 22, similar to that described above for apparatus 10. The plurality of sensors include at least a first sensor configured to detect a first type of signal from the body that is indicative of fetal or maternal activity during pregnancy or labour, and a second sensor configured to detect a second type of signal from the body, different from the first type of signal, that is also indicative of fetal or maternal activity during pregnancy or labour. The first and second sensors may be any combination of two different sensors selected from the group comprising an EMG sensor, a temperature sensor, and an accelerometer.

The monitoring device 22 may also comprise a third sensor to detect a third type of signal from the body that is indicative of fetal or maternal activity during pregnancy or labour. In some embodiments, the third type of signal may be the same as the first type of signal or the second type of signal. In other embodiments, the third type of signal may be different from the first and second types of signals. The third sensor may be selected from the group comprising an accelerometer, a temperature sensor, an EMG sensor and an ultrasound sensor, for example.

The monitoring device 22 may also comprise yet further sensors, e.g., any combination of four or more sensors, with at least two sensors being configured to detect a different type of signal. The further sensors may be selected from the group comprising an accelerometer, a temperature sensor, an EMG sensor and an ultrasound sensor, for example.

Referring to the embodiment depicted in FIG. 6a, the monitoring device 22 comprises four sensors, three of which are configured to detect different types of signals. In particular, the monitoring device 22 includes two EMG sensors 29, 30, a temperature sensor 102 and an accelerometer 103, all integrated into the monitoring device 22. One of the three different sensors, such as one of the EMG sensors 29, 30, can be considered to provide a first sensor that is configured to detect a first type of signal from the body indicative of fetal or maternal activity during pregnancy or labour. Another of the sensors, such as the temperature sensor 102 or accelerometer 103, can be considered to provide a second sensor that is configured to detect a second type of signal from the body, different from the first type of signal, but again indicative of fetal or maternal activity during pregnancy or labour.

Each of the EMG sensors 29, 30 includes a pair of contact points 29a, 29b, 30a, 30b disposed at the end portions 26a, 26b, 26c, 26d. Each of the contact points 29a, 29b, 30a, 30b can be considered to provide an EMG electrode. However, in this embodiment, the contact points 29a, 29b, 30a, 30b are each configured to receive and electrically couple to a respective removable EMG surface electrode 291a, 291b, 301a, 301b, as shown in FIG. 6b. The EMG surface electrodes 291a, 291b, 301a, 301b are configured to contact the skin via the openings 27a, 27b, 27c, 27d. The EMG sensors 29, 30 through electrical contact with the skin are configured to detect potential difference caused by uterine contractions.

The accelerometer 103 is disposed within the central portion 24 and is configured to monitor maternal and/or fetal movement. The temperature sensor 102 is also disposed within the central portion 24 and configured to track fluctuations in maternal temperature, in the same manner described above for apparatus 10.

The monitoring device 22 also comprises flex sensors 104a, 104b, 104c 104d in this embodiment, the flex sensors are disposed within respective flexible arm portions 25a, 25b, 25c, 25d of the monitoring device 22, for example. The flex sensors 104a, 104b, 104c 104d may be configured to detect bending or flexing of the arm portions 25a, 25b, 25c, 25d. Bending or flexing or other or related deformations such as stretching and contracting of the arm portions 25a, 25b, 25c, 25d may arise due to maternal movement, such as abdominal movement caused by baby movement, for example.

The flex sensors are usable as position sensors that can monitor the relative positioning of two or more of the EMG electrodes provided by the contact points 29a, 29b, 30a, 30b and/or the EMG surface electrodes 291a, 291b, 301a, 301b attached to the contact points 29a, 29b, 30a, 30b, during the fetal or maternal activity. The bending or flexing of the arm portions 25a, 25b, 25c, 25d coincides with relative movement of the respective EMG electrodes. A change in the relative position of the EMG electrodes, when the EMG electrodes are fixed to the abdomen using the adhesive seals 28a, 28b, 28c, 28d, for example, will cause flexing or bending or other deformation of the arm portions 25a, 25b, 25c, 25d. The flexing or bending or other deformation of the arm portions is indicative of deformation of the body, e.g. abdomen, during the fetal or maternal activity.

As an alternative to flex sensors, stretch sensors may be used. In general, any sensors that can allow changes in shape and/or dimensions of portions of the apparatus structure, e.g. the monitoring device, to be detected, which change in shape and/or dimensions result in relative movement of the EMG electrodes supported by the structure, may be used as position sensors.

The central portion 24 can also be fixed, e.g. adhered, to the abdomen. The central portion 24 can provide a reference location of the monitoring device, e.g. at a centre 241 of the central portion 24. Thus the electrodes and the reference location may retain respective fixed positions relative to the body.

While the electrodes and central portion 24 can be fixed to the body, the arm portions 25a, 25b, 25c, 25d therebetween are spaced from the body.

By monitoring the position of the EMG electrodes during the fetal or maternal activity, the EMG signals obtained from those electrodes can be interpreted in light of their relative positioning, enabling a more holistic analysis of the generated data. For example, it can enable the EMG signal changes to be correlated with a distortion in the body adjacent the monitoring device, the distortion occurring as a result of contractions or other maternal or fetal activity.

Figure 7A:
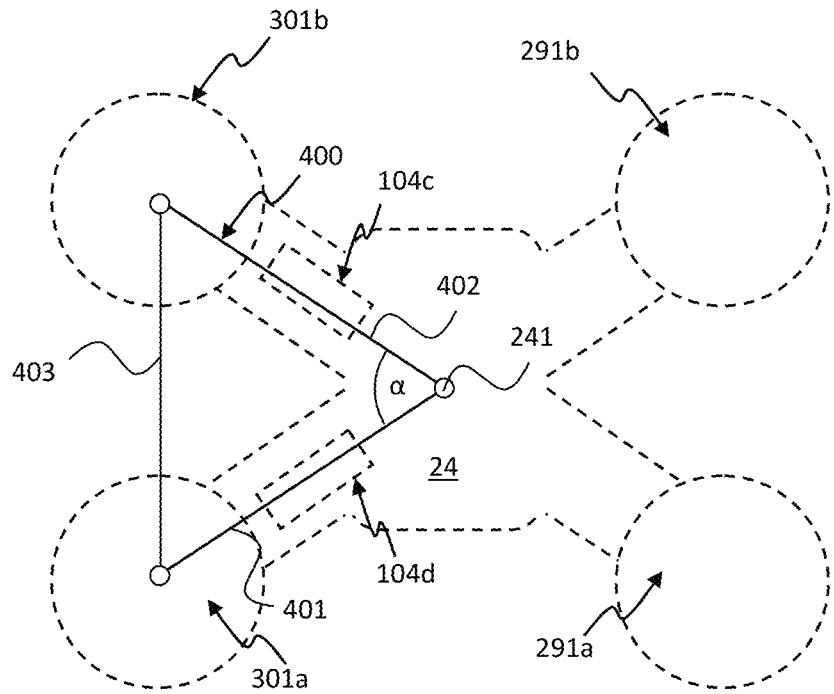
FIGS. 7a and 7b show simplified bottom views of the apparatus of FIG. 6b with EMG electrodes in first and second positions, respectively.

The relative positioning of the EMG electrodes can be determined based on a trigonometrical calculation. Referring to FIG. 7a, the length between a first one of the EMG electrodes 301a and the reference location 241 can provide a first side 401 of a notional triangle 400, the length between a second one of the EMG electrodes 301b and the reference location 241 can provide a second side 402 of the notional triangle 400, and the length between the two electrodes 301a, 301b can provide a third side 403 of the notional triangle.

Figure 7B:
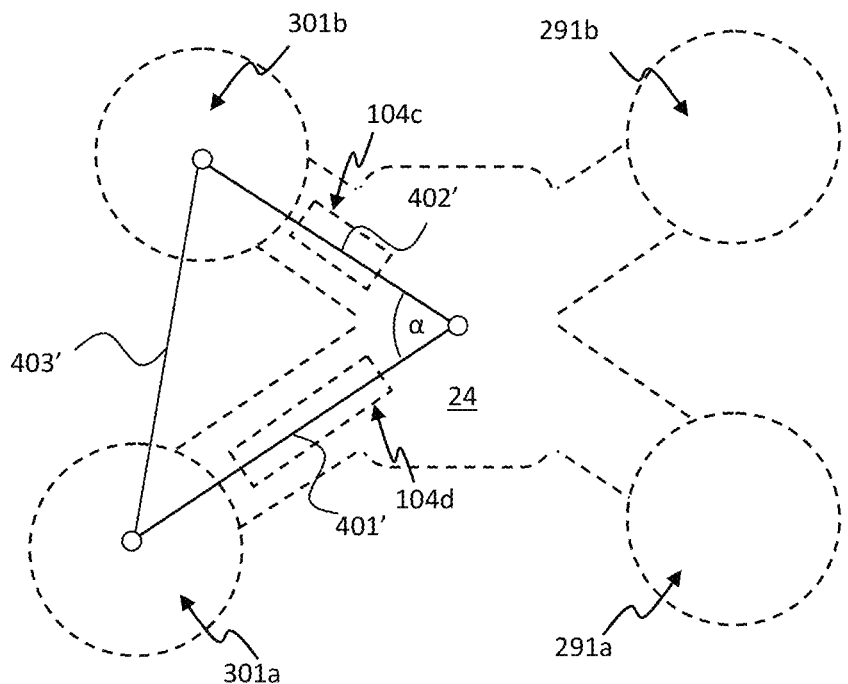

Upon maternal or fetal movement, the EMG electrodes 301a, 301b can move to new relative positions, as represented in FIG. 7b for example. The movement is reflected by flexing or bending of the arm portions and thus a change in geometry of the notional triangle 400', with, in this example, the first side 401' of the triangle increasing in length and the second side 402' of the triangle decreasing in length.

The flexing or bending of the arm portions is sensed by the flex sensors 104c, 104d enabling the distances between the electrodes 301a, 301b and the central portion 24 (and thus the lengths of the first and second sides 401, 401', 402, 402' of the notional triangle 400, 400') to be determined.

The angle α between the first and second sides 401, 401', 402, 402' can be a substantially fixed angle, e.g. if the flexible arm portions are only flexible in a length direction, and/or may be determined based on monitoring of flex of the arm portions in two or more dimensions. The third side 403, 403' of the notional triangle, and thus the distance between the two electrodes 301a, 301b, can be calculated from knowledge of the lengths of the first and second sides 401, 401', 402, 402' and their relative angle α. Nevertheless, other types of calculations may be made to monitoring the electrode positioning based on data from the position sensors. Moreover, the relative position may be determined between any combination of the EMG electrodes 291a, 291b, 301a, 301b using the technique described. Monitoring of the positioning may be carried out in real time in some embodiments and directly correlated with signals from other sensors, e.g. the signals as represented in FIGS. 4a to 4c.

Referring again to FIG. 6a, the apparatus 21 may also comprise at least one reference sensor 31 coupled to the monitoring device 22, similar to that described for apparatus 10. The at least one reference sensor 31 may be adapted to be placed on the body in a location spaced from the monitoring device 22, where fetal or maternal activity will be absent, so as to provide a reference to EMG readings and enable filtering of the signals occurring due to fetal or maternal activity from signals derived from other sources, such as gross body movement (e.g. walking, turning in bed, etc.) or normal temperature fluctuations. In some embodiments, the at least one reference sensor 31 may be placed at the ribs. It will be appreciated however that the at least one reference sensor 31 may be placed elsewhere on the body, such as at the hip or sternum, for example. The at least one reference sensor 31 is positioned externally to the housing of the monitoring device 22 and is be movable relative to the housing. The at least one reference sensor 31 is connected via a wire that retains a physical and electrical connection between the reference sensor and the other components of the monitoring device 22 but may be wirelessly connected in alternative embodiments.

In some embodiments, the reference sensor 31 may be an EMG sensor of the type described above for apparatus 10. The reference sensor 31 may have a contact point 32 adapted to receive and electrically couple to a removable EMG surface reference electrode 311, as shown in FIG. 6b.

In the embodiment depicted in FIG. 6b, the reference sensor 31 may also be provided with an end portion 33 having an opening 34. An adhesive seal 35 may be provided on the perimeter of the opening 34. The adhesive seal 35 may be configured to adhere to the body so as to form a water-tight barrier around the opening 34. The EMG surface reference electrode 311 is configured to contact the skin via the opening 34. In this example, filtering of the signals occurring due to maternal or fetal activity may be achieved by subtracting the signal derived from the reference sensor 31 from the signal derived from any of the EMG sensors 29, 30 of the monitoring device 22.

The monitoring device according to any of the above embodiments may be adapted to be placed on the maternal abdomen located over the fundus of the uterus, for example. The present disclosure recognises that the area of greatest traceable maternal or fetal activity during a contraction is over the fundus. It will be appreciated however that the monitoring device may be placed elsewhere on the body where useful monitoring of fetal or maternal activity may be conducted. The design and shape of the monitoring device may make it suitable for placement in a relatively intuitive and straightforward manner at the appropriate location, e.g. at the fundus of the maternal abdomen. The monitoring device may be configured for operation by a number of stakeholders, such as a clinician, patient, partner or aid worker and may be relatively easy to locate and operate.

The apparatus according to any of the above embodiments may also comprise a user interface coupled to the monitoring device, the user interface comprising a display for displaying information derived from the signals detected by the plurality of sensors. The user interface comprises one or more of a desktop computer, a laptop computer, a smartphone, a personal digital assistant, a watch, a data collection band and other devices of the like configured to display the information. The monitoring device may communicate with the user interface via a communications network, e.g. via the internet, Wi-Fi, Bluetooth, or otherwise. In some embodiments, the user interface may be remotely located so as to be accessible by a clinician. This can allow patients to be monitored without requiring the clinician to be present. Additionally or alternatively, the apparatus may comprise a user interface integrated into the monitoring device. For example, the user interface may be an on-board indicator. The user interface may provide an indication of the type of data being collected by the monitoring device and/or indication about the attachment status of the device to the body, power levels or otherwise.

Figure 8A:
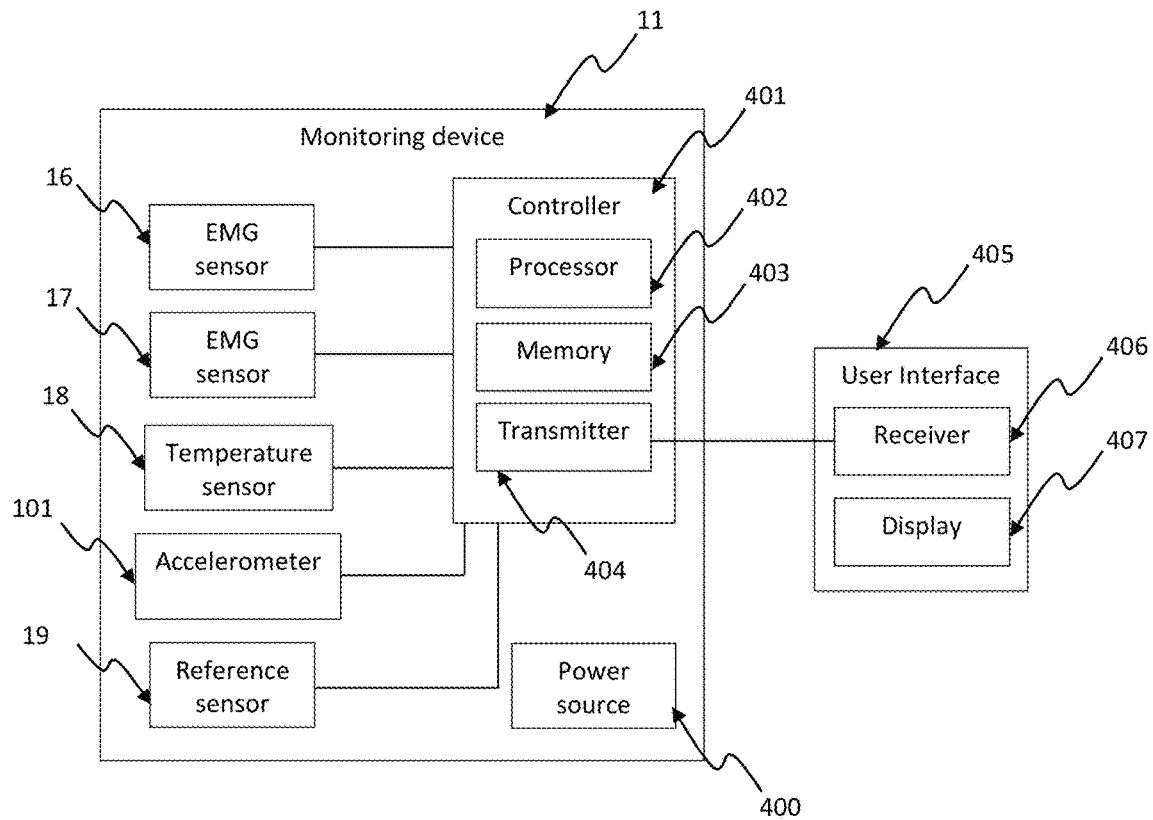
FIGS. 8a and 8b are schematic illustrations of various electronic components of the apparatus of FIG. 1 and FIG. 5, respectively.

A schematic illustration of various electronic components of the apparatus is shown in FIG. 8a. The operation of the electronic components may be applied to any of the embodiments of the apparatus described above. However, in this particular embodiment, the schematic illustration of FIG. 8 will be described with reference to the apparatus 10 of FIG. 1. The monitoring device 11 may comprise a power source 400, e.g., a battery, to power electronic components of the monitoring device 11. The monitoring device 11 may also comprise a controller 401 (e.g. a microcontroller) that is connected to the plurality of sensors of the monitoring device 11. The plurality of sensors of the monitoring device 11 include the two EMG sensors 16, 17, the temperature sensor 18 and the accelerometer 101. The apparatus 10 also includes the reference sensor 19.

The controller 401 includes a processor 402 that receives signals from the plurality of sensors 16, 17, 18, 101 as well as the reference sensor 19, and stores the signals in memory 403. The processor 402 may optionally filter the signals detected by the plurality of sensors 16, 17, 18, 101 based on the signal detected by the reference sensor 19. A transmitter 404 transmits information derived from the signals detected by the plurality of sensors 16, 17, 18, 101 and/or the reference sensor 19 to a user interface 405, by virtue of a wireless signal, for example. Radiofrequency signals or Bluetooth signals, etc., which contain the information, may be transmitted from the monitoring device 11 to the user interface 405. The user interface 405 has a receiver 406 that receives the information from the controller 401, and a display 407 that displays the information. The information may be presented in a format that is identifiable and assessable by a clinician so as to facilitate or assist in monitoring pregnancy or labour. Alternatively, the information may be presented in a simpler format for the patient to monitor their own pregnancy or labour in the absence of a clinician.

Figure 8B:
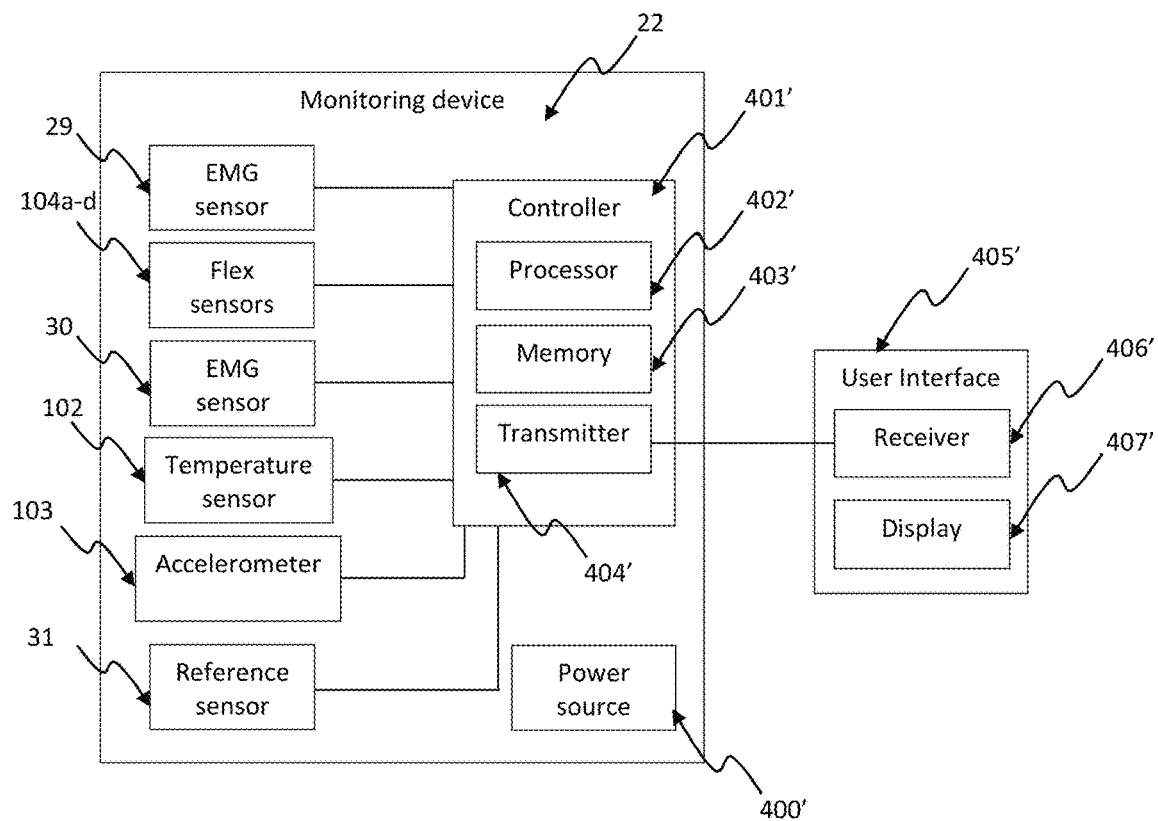

A further schematic illustration of various electronic components is shown in FIG. 8b. In this particular embodiment, the schematic illustration corresponds to the apparatus 21 of FIG. 5. The apparatus is substantially the same from an electrical perspective as the apparatus 10 as described with reference to FIG. 8a. However, the flex sensors 104a-d are additionally provided, which are connected to the controller 401', the controller including the processor 402', memory 403' and transmitter 404', the controller being connected to the user interface 405' including its receiver 406' and display 407'. In FIGS. 8a and 8b, connection between the various components, including between the monitoring devices and the user interfaces, for example, may be wired or wireless.

Generally, it will be recognised that any controller that is used in the present disclosure may comprise a number of control or processing modules for receiving and processing the signals derived from the plurality of sensors and may also include one or more storage elements, for storing data such as the types of signals. The modules and storage elements can be implemented using one or more processing devices and one or more data storage units, which modules and/or storage devices may be at one location or distributed across multiple locations and interconnected by one or more communication links.

Further, the modules can be implemented by a computer program or program code comprising program instructions. The computer program instructions can include source code, object code, machine code or any other stored data that is operable to cause the controller to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g., RAM) and/or non-volatile (e.g., ROM, disk) memory or otherwise.

In any of the above embodiments, the apparatus may comprise one or more roving sensors for providing additional vital diagnostic and prognostic information about pregnancy or labour. The roving sensors may be independent of the monitoring device. The roving sensors may include a fetal heart rate monitor, enabling a determination of fetal distress during maternal contraction, a maternal heart rate monitor, providing an indication of the overall health of the mother during pregnancy or labour, and/or an additional EMG sensor. The roving sensors may be coupled to the monitoring device and/or the user interface via a wired or wireless connection.

The embodiments described above can have numerous advantages. For example, the plurality of sensors provide a continual monitor of at least one type of signal, ensuring that no data is missed or lost, thus providing accurate collection of data. Further, the combination of sensors may assist in assessing the status of pregnancy and labour, for example distinguishing between false labour and the onset of labour, monitoring the health of the mother during pregnancy or labour, and/or monitoring the health of the fetus before or during labour. Further, the embodiments may allow patients to operate the monitoring device without the need for trained clinicians to be present, thus allowing monitoring to occur in places other than a hospital setting.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An apparatus for monitoring pregnancy or labour, the apparatus comprising:
   an electromyography sensor comprising two or more EMG electrodes to monitor fetal or maternal activity during pregnancy or labour;
   one or more position sensors to monitor the relative positioning of the two or more EMG electrodes during the fetal or maternal activity;
   a monitoring device, the electromyography sensor and the one or more position sensors being comprised in the monitoring device; and
   wherein the one or more position sensors comprise one or more flex or stretch sensors that monitor flexing, bending or deformation of a portion of the monitoring device to determine the relative positioning of the two or more EMG electrodes.

2. The apparatus of claim 1, comprising adhesive to adhere the EMG electrodes to a body.

3. The apparatus of claim 1 wherein the monitoring device comprises a central portion and one or more flexible arm portions extending from the central portion, and wherein each of the one or more flexible arm portions are configured to be manipulable relative to the central portion, the position sensors monitoring flexing or bending of the arm portions.

4. The apparatus of claim 3, comprising adhesive to adhere the central portion to a body.

5. The apparatus of claim 3, wherein the monitoring device comprises at least four of the flexible arm portions arranged in a cross-configuration.

6. The apparatus of claim 3, wherein one of the EMG electrodes is located at an end portion of each of the arm portions.

7. The apparatus of claim 3, wherein the one or more position sensors are located in the arm portions.

8. The apparatus of claim 3, wherein each arm portion has an end portion with an opening, and an adhesive seal provided on the perimeter of the opening, wherein the adhesive seal is configured to adhere to a body so as to secure the monitoring device to the body and to form a water-tight barrier around the opening.

9. The apparatus of claim 1 further comprising a temperature sensor and/or an accelerometer.

10. The apparatus of claim 9, wherein the monitoring device comprises a central portion and one or more flexible arm portions extending from the central portion, and wherein each of the one or more flexible arm portions are configured to be manipulable relative to the central portion, the position sensors monitoring flexing or bending of the arm portions and, wherein the temperature sensor and/or the accelerometer are disposed within the central portion.

11. An apparatus for monitoring pregnancy or labour, the apparatus comprising:
    a monitoring device comprising:
    a central portion and a plurality of flexible arm portions extending from the central portion, and wherein each of flexible arm portions are configured to be manipulable relative to the central portion;
    an electromyography sensor comprising two or more EMG electrodes to monitor fetal or maternal activity during pregnancy or labour, each EMG electrode located at an end portion of a respective one of the flexible arm portions; and
    a flex or stretch sensor located in each arm portion.

12. The apparatus of claim 11, wherein the monitoring device comprises at least four of the flexible arm portions arranged in a cross-configuration.

13. The apparatus of claim 11, wherein the monitoring device further includes an ultrasound sensor.

14. The apparatus of claim 11, wherein the fetal activity comprises one or more of: fetal positioning, fetal movement and fetal heart rate.

15. The apparatus of claim 11, wherein the maternal activity comprises one or more of: muscle and uterine contractions, maternal positioning, maternal movement, maternal heart rate and maternal temperature.

16. The apparatus of claim 11, wherein the monitoring device comprises a housing to house electronic components therein.

17. The apparatus of claim 16, wherein the housing is a sealed housing so as to prevent fluid ingress.

18. The apparatus of claim 16, wherein the housing comprises a top surface and a contoured bottom surface adapted for placement on the body.

19. The apparatus of claim 16, wherein the electromyography sensor comprises at least one electrical contact disposed on the bottom surface of the housing, the at least one electrical contact is configured to receive and electrically couple to an EMG surface electrode, the at least one electrical contact is also configured to protrude from the bottom surface such that the bottom surface is spaced from the body when the monitoring device is placed on the body.

20. The apparatus of claim 16, wherein a temperature sensor is disposed on the bottom surface of the housing and an accelerometer is disposed within the housing.

21. The apparatus of claim 16, wherein an end portion of each of the flexible arm portions has an opening, and an adhesive seal provided on the perimeter of the opening, wherein the adhesive seal is configured to adhere to the body so as to secure the monitoring device to the body and to form a water-tight barrier around the opening.

22. The apparatus of claim 11, wherein the electromyography sensor comprises at least one electrical contact disposed at a respective end portion, the at least one electrical contact is configured to receive and electrically couple to an EMG surface electrode.

23. The apparatus of claim 11, wherein the monitoring device further includes a temperature sensor and an accelerometer, and wherein the temperature sensor and the accelerometer are disposed within the central portion.

24. The apparatus of claim 11, wherein the monitoring device is adapted to be placed on the abdomen.

25. The apparatus of claim 24, wherein the monitoring device is adapted to be located over the fundus of the uterus.

26. The apparatus of claim 11, further comprising a user interface coupled to and/or comprised in the monitoring device for displaying information derived from the signals detected by the plurality of sensors.

27. The apparatus of claim 26, wherein the user interface comprises one or more of a desktop computer, a laptop computer, a smartphone, a personal digital assistant, a watch, a data collection band and other devices of the like configured to display the information.

28. The apparatus of claim 11, comprising at least one reference sensor adapted to be placed on the body in a location spaced from the monitoring device, where fetal or maternal activity will be absent, so as to provide a reference to the plurality of sensors, the reference sensor being connected to the monitoring device by wires or wirelessly.

29. The apparatus of claim 28, wherein the at least one reference sensor is adapted to be placed at the ribs.

30. The apparatus of claim 28, wherein the at least one reference sensor is adapted to be placed at the hip or sternum.

31. The apparatus of claim 28, wherein the at least one reference sensor comprises one or more of an electromyography sensor, a temperature sensor, an accelerometer and an ultrasound sensor.

32. The apparatus of claim 11, further comprising one or more roving sensors independent of the monitoring device.

33. The apparatus of claim 32, wherein the one or more roving sensors comprises a fetal heart rate monitor and/or a maternal heart rate monitor.

34. The apparatus of claim 32, wherein the one or more roving sensors comprises an electromyography sensor.

35. An apparatus for monitoring pregnancy or labour, the apparatus comprising:
   a monitoring device to be placed on a body and comprising a plurality of sensors integrated into the monitoring device, the plurality of sensors including at least:
   a first sensor configured to detect a first type of signal from the body indicative of a first type of fetal or maternal activity during pregnancy or labour; and
   a second sensor configured to detect a second type of signal from the body, different from the first type of signal, also indicative of the first type of fetal or maternal activity during pregnancy or labour, wherein the first sensor is an electromyography sensor and the second sensor is a temperature sensor.

36. The apparatus of claim 35, wherein the monitoring device comprises a housing to house electronic components therein.

37. The apparatus of claim 36, wherein the electromyography sensor comprises at least one electrical contact disposed on the bottom surface of the housing, the at least one electrical contact is configured to receive and electrically couple to an EMG surface electrode, the at least one electrical contact is also configured to protrude from the bottom surface such that the bottom surface is spaced from the body when the monitoring device is placed on the body.

38. The apparatus of claim 36, wherein the temperature sensor is disposed on the bottom surface of the housing and an accelerometer is disposed within the housing.

39. The apparatus of claim 36, wherein the monitoring device comprises a central portion and one or more flexible arm portions extending from the central portion, and wherein each of the one or more flexible arm portions are configured to be manipulable relative to the central portion so as to facilitate placement of the monitoring device on the body, wherein an end portion of each of the flexible arm portions has an opening, and an adhesive seal provided on the perimeter of the opening, wherein the adhesive seal is configured to adhere to the body so as to secure the monitoring device to the body and to form a water-tight barrier around the opening.

40. The apparatus of claim 39, wherein the temperature sensor and the accelerometer are disposed within the central portion.

41. The apparatus of claim 35, wherein the monitoring device further includes an ultrasound sensor.

42. The apparatus of claim 35, wherein the monitoring device further includes an accelerometer.

43. The apparatus of claim 35, wherein the electromyography sensor comprises at least one electrical contact disposed at a respective end portion, the at least one electrical contact is configured to receive and electrically couple to an EMG surface electrode.

44. The apparatus of claim 35, further comprising at least one reference sensor adapted to be placed on the body in a location spaced from the monitoring device, where fetal or maternal activity will be absent, so as to provide a reference to the plurality of sensors, the reference sensor being connected to the monitoring device by wires or wirelessly.

45. The apparatus of claim 35, further comprising one or more roving sensors independent of the monitoring device.

46. An apparatus for monitoring pregnancy or labour, the apparatus comprising:
   a monitoring device to be placed on a body and comprising a plurality of sensors integrated into the monitoring device, the plurality of sensors including at least:
   a first sensor configured to detect a first type of signal from the body indicative of a first type of fetal or maternal activity during pregnancy or labour; and
   a second sensor configured to detect a second type of signal from the body, different from the first type of signal, also indicative of the first type of fetal or maternal activity during pregnancy or labour, wherein the first sensor is a temperature sensor and the second sensor is an accelerometer.

47. The apparatus of claim 46, wherein the monitoring device further includes an ultrasound sensor.

48. The apparatus of claim 46, wherein the monitoring device comprises a housing to house electronic components therein.

49. The apparatus of claim 48, wherein the housing comprises a top surface and a contoured bottom surface adapted for placement on the body.

50. The apparatus of claim 49, wherein the temperature sensor is disposed on the bottom surface of the housing and the accelerometer is disposed within the housing.

51. The apparatus of claim 49, wherein the monitoring device comprises a central portion and one or more flexible arm portions extending from the central portion, and wherein each of the one or more flexible arm portions are configured to be manipulable relative to the central portion so as to facilitate placement of the monitoring device on the body, wherein an end portion of each of the flexible arm portions has an opening, and an adhesive seal provided on the perimeter of the opening, wherein the adhesive seal is configured to adhere to the body so as to secure the monitoring device to the body and to form a water-tight barrier around the opening.

52. The apparatus of claim 46, comprising at least one reference sensor adapted to be placed on the body in a location spaced from the monitoring device, where fetal or maternal activity will be absent, so as to provide a reference to the plurality of sensors, the reference sensor being connected to the monitoring device by wires or wirelessly.

53. The apparatus of claim 46, further comprising one or more roving sensors independent of the monitoring device.

54. The apparatus of claim 53, wherein the one or more roving sensors comprises a fetal heart rate monitor and/or a maternal heart rate monitor.

55. The apparatus of claim 53, wherein the one or more roving sensors comprises an electromyography sensor.

56. A method of monitoring pregnancy or labour, the method comprising:
   placing a monitoring device on a body, the monitoring device comprising an electromyography sensor comprising two or more EMG electrodes and one or more position sensors;
   monitoring fetal or maternal activity during pregnancy or labour using the EMG electrodes of the electromyography sensor; and
   monitoring the relative positioning of the two or more EMG electrodes during the fetal or maternal activity using the one or more position sensors, wherein the one or more position sensors comprise one or more flex or stretch sensors that monitor flexing, bending or deformation of a portion of the monitoring device to determine the relative positioning of the two or more EMG electrodes.

57. An apparatus for monitoring pregnancy or labour, the apparatus comprising:
   a monitoring device to be placed on a body and comprising a plurality of sensors integrated into the monitoring device, the plurality of sensors including at least:
      a first sensor configured to detect a first type of signal from the body indicative of a first type of fetal or maternal activity during pregnancy or labour; and
      a second sensor configured to detect a second type of signal from the body, different from the first type of signal, also indicative of the first type of fetal or maternal activity during pregnancy or labour;
   wherein the monitoring device comprises a housing to house electronic components therein;
   wherein the housing is a sealed housing so as to prevent fluid ingress.

* * * * *